United States Patent [19]
Rheinberger et al.

[11] Patent Number: 5,886,212
[45] Date of Patent: Mar. 23, 1999

[54] MULTIFUNCTIONAL VINYL CYCLOPROPANE DERIVATIVES

[75] Inventors: Volker Rheinberger; Frank Zeuner, both of Vaduz; Norbert Moszner, Eschen, all of Liechtenstein

[73] Assignee: Ivoclar AG, Liechtenstein

[21] Appl. No.: 818,849

[22] Filed: Mar. 17, 1997

[30] Foreign Application Priority Data

Mar. 18, 1996 [DE] Germany .................. 196 12 004.7

[51] Int. Cl.[6] .................. C07C 69/743; C08F 32/02
[52] U.S. Cl. .................. 560/124; 560/125; 526/308; 526/309
[58] Field of Search .................. 560/124, 125; 526/308, 309

[56] References Cited

U.S. PATENT DOCUMENTS

| | | | |
|---|---|---|---|
| 4,321,406 | 3/1982 | Fayter, Jr. .................. | 560/124 |
| 4,713,478 | 12/1987 | Fayter, Jr. .................. | 560/124 |
| 4,713,479 | 12/1987 | Clark, Jr. et al. .................. | 560/124 |

*Primary Examiner*—Tae Yoon
*Attorney, Agent, or Firm*—Nixon, Hargrave, Devans & Doyle LLP

[57] ABSTRACT

Multifunctional polymerizable vinyl cyclopropane derivatives are described which have at least two vinyl cyclopropane units and are suitable in particular as a constituent of dental materials.

5 Claims, No Drawings

MULTIFUNCTIONAL VINYL CYCLOPROPANE DERIVATIVES

The invention relates to multifunctional vinyl cyclopropane derivatives, a process for the preparation thereof, the use thereof in particular as a dental material, a dental material containing them, and to polymers and copolymers obtainable therefrom.

Substituted vinyl cyclopropanes are known from the state of the art. Thus, T. Takahashi et al. describe in J. Polym. Sci., Part B, 3 (1965), 251 that 1,5-ring-opened compounds form during the radical polymerization of vinyl cyclopropanes and that radical-stabilizing substituents are promoting the ring opening in the 1-position.

It has furthermore been shown that 1,1-disubstituted 2-vinyl cyclopropanes, such as the liquid 1,1-bis (ethoxycarbonyl)- or 1,1-dicyano-2-vinyl cyclopropane, show somewhat less volume shrinkage on polymerization compared with conventional vinyl monomers, such as acrylonitrile or methyl methacrylate. However, volume expansion was also recorded for a specially substituted vinyl cyclopropane, namely 1,1-bis(phenoxycarbonyl)-2-vinyl cyclopropane, after radical polymerization (cf J. Sugiyama et al., Macromolecules 27 (1994), 5543).

Known ring-opening monomers, such as methylene group-containing spiro orthocarbonates, spiro orthoesters or bicyclic orthoesters (cf R. K. Sadhir et al., Expanding Monomers, CRC Press, Boca Raton 1992), are generally moisture-sensitive, are accessible only by complicated syntheses and can be processed by radical polymerization only into polymers having a low molecular weight. Furthermore, the radical polymerization of spiro orthocarbonates or spiro orthoesters results in polymers having carbonate-ether groups or ester-ether groups in the main chain. These groups are, however, easily cleavable by hydrolysis or by enzymes so that these polymers are not very stable under corresponding conditions. 1,1-disubstituted 2-vinyl cyclopropanes known hitherto have in most cases only one group capable of polymerization, with the result that their polymerization compared with polymerization of customary cross-linking monomers, e.g. based on di(meth)acrylates, only polymers having poorer mechanical properties can be produced. Vinyl cyclopropanes with two groups capable of polymerization, such as 1-vinyl-6,7-benzo-4,9-dioxaspiro[2.6]nonane (cf F. Sanda et al., Macromolecules 27 (1994), 1099) or 1,10-bis (vinyl)-4,8,12,15-tetraoxatrispiro[2.2.2.2.2]pentadecane (cf T. Okazaki et al., Macromolecules 28, (1995) 6026), which are cyclic acetals having vinyl cyclopropane groups, are indeed known, but on radical polymerization they likewise result in polymers having hydrolytically or enzymatically cleavable ester bonds in the main chain.

The object of the invention is accordingly to make available vinyl cyclopropanes which are radically polymerizable, result in crosslinked polymers due to their multifunctionality, form polymers which bear no hydrolytically cleavable groups in the main chain, and can be used in particular as a component of dental materials.

This object is achieved by the multifunctional vinyl cyclopropane derivatives of the present invention.

The subject matter of the present invention is also the process for the preparation of the multifunctional vinyl cyclopropane derivatives, the use thereof, a dental material containing the multifunctional vinyl cyclopropane derivatives, and polymers and copolymers of the multifunctional vinyl cyclopropane derivatives.

The multifunctional vinyl cyclopropane derivatives according to the invention are compounds of the following general formula (I) stereoisomers thereof and mixtures of such stereoisomers

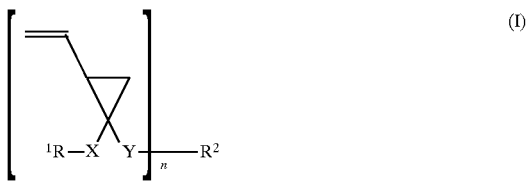

where $R^1$, $R^2$, $R^3$, $R^4$, X, Y and n independently of one another have the following meanings:

$R^1$=H, substituted or unsubstituted $C_1$ to $C_{12}$ alkyl or substituted or unsubstituted $C_6$ to $C_{14}$ aryl;

$R^2$=n-times substituted $C_1$ to $C_{20}$ alkylene which can be interrupted by O, S, N or NH, or n-times substituted $C_6$ to $C_{14}$ arylene;

X=CO, CO—O, CO—S, CO—$NR^3$, $SO_2$ or is absent, where $R^3$=H, $C_1$ to $C_6$ alkyl or $C_6$ $C_{14}$ aryl;

Y=CO, CO—O, CO—S, CO—$NR^4$ or $SO_2$, where $R^4$=H, $C_1$ to $C_6$ alkyl or $C_6$ to $C_{14}$ aryl; and n=2 to 6.

The above formula (I) covers only those compounds which are compatible with the valence therory.

The alkylene group which is possible as $R^2$ may be interrupted, e.g. by O that is it comprises in its carbon chain the moiety . . . C—O—C . . .

Further, the alkyl and alkylene groups may be linear, branched or cyclic.

The substituents optionally present in the case of the radical $R^1$ are in particular OH, halogen, $C_1$ to $C_6$ alkoxy or COOH and it also possible for $R^1$ to be substituted several times. If several substituents are present, these may be chosen independently of one another.

In the general formula (I), the index n means that the group $R^2$ is substituted n times by the substituted vinyl cyclopropane radical given in brackets.

Moreover, preferred definitions which can be chosen independently of one another exist for the above-mentioned variables of formula (I), these definitions being as follows:

$R^1$=H, substituted or unsubstituted $C_1$ to $C_6$ alkyl or substituted or unsubstituted $C_6$ aryl;

$R^2$=n-times substituted $C_1$ to $C_{12}$ alkylene, $C_6$ to $C_{14}$ arylene or $C_6$ to $C_8$ cycloalkylene;

X=CO—C;

$R^3$=H or $C_1$ to $C_3$ alkyl;

Y=CO—C;

$R^4$=H or $C_1$ to $C_3$ alkyl; and/or n=2 or 3.

Preferred compounds are, therefore, those in which at least one of the variables of formula (I) has the preferred definition described above.

The vinyl cyclopropane derivatives according to the invention are usually present as stereoisomer mixtures and in particular as racemates.

In order to prepare the multifunctional vinyl cyclopropane derivatives according to the invention, the following process is used: a monovinyl cyclopropane derivative of the formula (IIA)

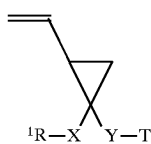
(IIA)

is reacted with an n-times functionalized coupling component of the formula (IIB)

$$Z_nR^2 \quad (IIB)$$

under formation of the multifunctional vinyl cyclopropane derivatives of the formula (I), where T=H or halogen and Z=a leaving group and the remaining variables are defined as above.

Preferred examples of the leaving group Z are OH, $NH_2$ or halogen.

The preparation process according to the invention can accordingly be explained by means of the reaction equation below.

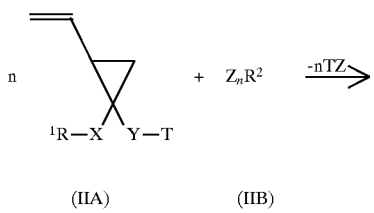

Compounds of the formula (IIA) can be prepared according to the process known for the preparation of vinyl cyclopropanes (cf U.S. Pat. No. 4,713,478 and U.S. Pat. No. 4,713,479) of reacting trans-4-dihalobut-2-enes with corresponding derivatives of malonic acid, where optionally educts provided with protective groups have to be used. This process is illustrated by the equations below with reference to an example.

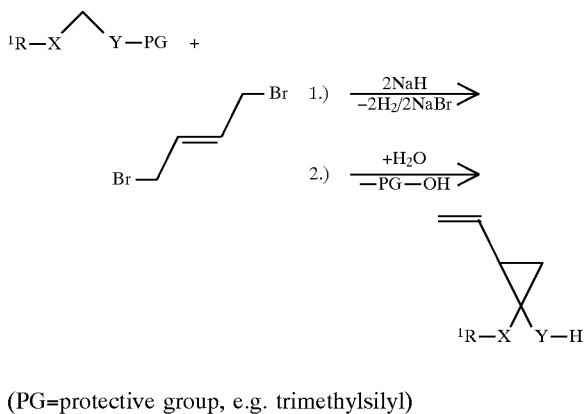

(PG=protective group, e.g. trimethylsilyl)

and optionally

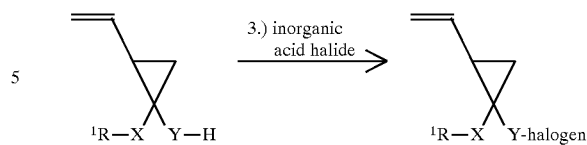

The difunctional vinyl cyclopropane (4), for example, can be obtained by means of the process according to the invention by esterification of resorcinol with 1-methoxycarbonyl-1-chloroformyl-2-vinyl cyclopropane, in accordance with the reaction equation below:

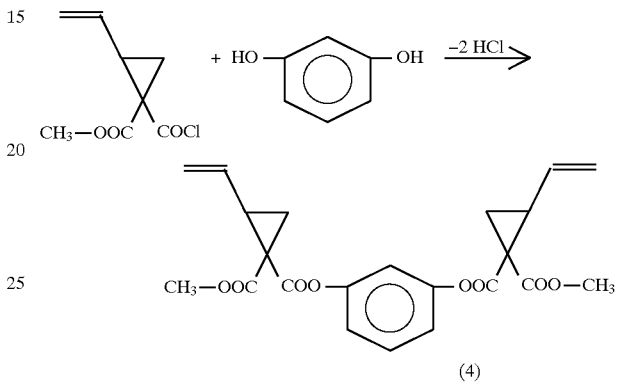

Furthermore, the difunctional vinyl cyclopropane (3), for example, can be obtained by means of the process according to the invention by esterification of ethylene glycol with 2-vinyl cyclopropane-1,1-dicarboxylic acid monomethyl ester which, for its part, is obtainable by reaction of commercial malonic acid dimethyl ester with trans-1,4-dibromobut-2-ene and subsequent partial saponification of the formed 2-vinyl cyclopropane-1,1-dicarboxylic acid dimethyl ester, in accordance with the reaction equation below:

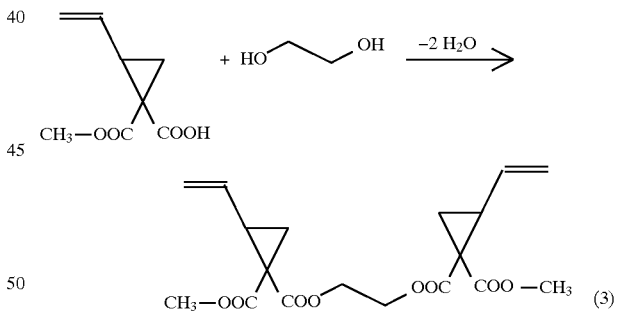

The coupling component (IIB) can be, in particular, bi- or polyvalent hydroxy compounds, such as ethylene glycol, di- or triethylene glycol, butylene glycol, 1,6-hexanediol, glycerol, triethanolamine, trimethylolpropanetriol, pentaerythritol or glucose, and hydroquinone, resorcinol, pyrocatechol or pyrogallol.

In addition, di- or multifunctional amines, such as ethylene diamine, propylene diamine, hexamethylene diamine and o-, p- or m-phenylene diamine, are also suitable.

Furthermore, it is also possible to use, in particular, as the coupling component (IIB) di- or multifunctional organic halogen compounds, such as 1,2-dibromoethane, 1,4-dibromobutane, 1,10-dibromodecane, 1,2,3-tribromopropane, 1,4-dibromobenzene or 1,3,5-tribromobenzene. These halogen compounds can be reacted e.g. with the sodium salt of the vinyl cyclopropane-1,1-dicarboxylic acid monomethyl ester to form the corresponding vinyl cyclopropane derivative according to the invention in accordance with the reaction equation below.

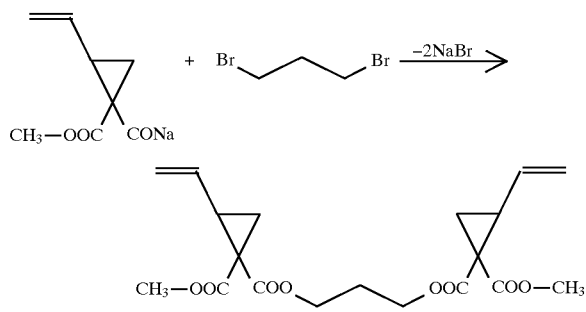

In addition to the process described previously, it is also possible to prepare in the first step, by reacting the compound (IIIA) with n-times functionalized coupling component (IIB), an intermediate (IIIB) which is then converted by reaction with 1,4-dibromobut-2-ene into an n-times functional vinyl cyclopropane derivative (I) according to the invention, as shown by the following reaction equations:

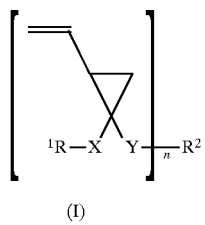

(I)

Preferred examples of the compound (IIIA) are derivatives of malonic acid.

In this way, e.g. the difunctional vinyl cyclopropane (4) can be prepared by initially esterifying resorcinol with malonic acid monomethyl ester chloride and subsequently reacting the formed ester with 1,4-dibromobut-2-ene, as shown by the reaction equations below:

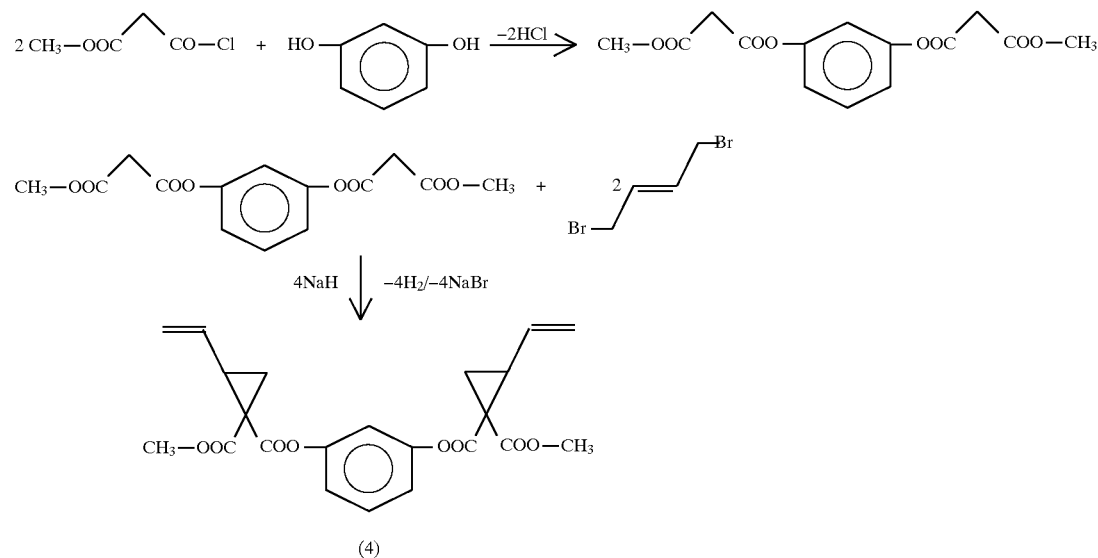

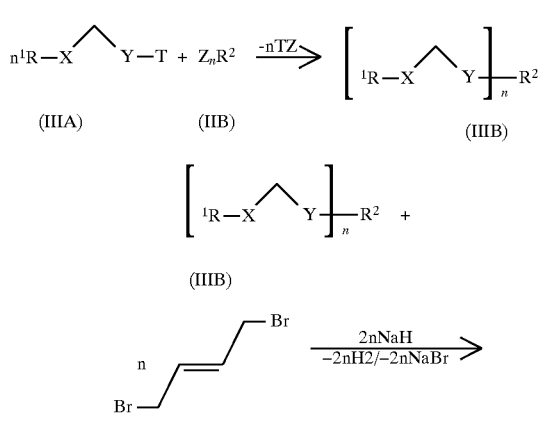

Due to the presence of polymerizable groups, the multifunctional vinyl cyclopropane derivatives according to the invention are suitable as starting materials for the preparation of polymers and copolymers. They can be homopolymerized using the known methods of radical polymerization or copolymerized e.g. with suitable comonomers. When conventional radical initiators are used, there is a very extensive formation of polymers and copolymers with ring-opened 1,5-structures, which often results in a reduction in polymerization shrinkage.

The radical polymerization is conducted using the known radical initiators (cf Encyclopedia of Polymer Science and Engineering, Vol. 13, Wiley-Interscience Publisher, New York 1988, pages 754 et seq.). For this purpose azo compounds, such as azobis(isobutyronitrile) (AIBN) or azobis(4-cyano-valeric acid), or peroxides, such as dibenzoyl peroxide, dilauroyl peroxide, tert.-butyl peroctoate, tert.-butyl perbenzoate or di-(tert.-butyl)-peroxide, are particularly suitable.

Benzpinacol and 2,2'-dialkylbenzpinacols are suitable above all as initiators for the hot-curing.

Furthermore, photoinitiators (cf J. P. Fouassier, J. F. Rabek (publisher), Radiation Curing in Polymer Science and Technology, Vol. II, Elsevier Applied Science, London and New York 1993) can also be used for the polymerization using UV light or visible-wavelength light, such as benzoin ethers, dialkylbenzil ketals, dialkoxyacetophenones, acyl phosphine oxides, α-diketones, such as 9,10-phenanthrenequinone, diacetyl, furil, anisil, 4,4'-dichlorobenzil and 4,4'-dialkoxybenzil and camphor quinone.

In order to accelerate the initiation by peroxides or α-diketones, combinations with aromatic amines can be used in particular. Moreover, redox systems can be used as accelerators, such as combinations of benzoyl peroxide, lauroyl peroxide or camphor quinone with amines, such as N,N-dimethyl-p-toluidine, N,N-dihydroxyethyl-p-toluidine or structurally related amines.

The vinyl cyclopropanes can be used in particular as a constituent of adhesives, cements, composites and moulded bodies and preferably of dental materials. It is possible for the vinyl cyclopropanes to be present in at least partially polymerized form. Further components with which the vinyl cyclopropanes can be combined are mentioned below.

The vinyl cyclopropane derivatives according to the invention can be polymerized singly or together with conventional radically polymerizable comonomers, in particular with difunctional cross-linking monomers. Particularly suitable comonomers for the preparation of adhesives or dental materials are above all cross-linking bi- or polyfunctional acrylates or methacrylates, such as bisphenol-A-di(meth)acrylate, addition products of methacrylic acid and bisphenol-A-diglycidyl ethers, urethane dimethacrylates, e.g. the addition product of hydroxyethyl methacrylate and 2,2,4-trimethylhexamethylene diisocyanate, di-, tri- or tetraethylene glycol di(meth)acrylate, decanediol di(meth)acrylate, trimethylolpropane tri(meth)acrylate, pentaerythritol tetra(meth)acrylate, butanediol di(meth)acrylate, 1,10-decanediol di(meth)acrylate and 1,12-dodecanediol di(meth)acrylate.

Moreover, the vinyl cyclopropane derivatives according to the invention or mixtures thereof with other monomers can be filled with organic or inorganic particles or fibres in order to improve the mechanical properties. Preferred inorganic particulate fillers are amorphous spherical materials based on mixed oxides of $SiO_2$, $ZrO_2$ and/or $TiO_2$, microfine fillers such as pyrogenic silica or precipitated silicas, and macro or mini fillers such as quartz powder, glass ceramic powder or glass powder having an average particle size of 0.01 to 5 $\mu$m, and X-ray-opaque fillers such as ytterbium trifluoride. Moreover, glass fibres, polyamide fibres or carbon fibres can also be used.

Finally, further components can also be added to the vinyl cyclopropane derivatives according to the invention, such as e.g. stabilizers, UV absorbers, dyes, pigments or lubricants.

The multifunctional vinyl cyclopropane derivatives according to the invention are suitable in particular as a constituent of dental materials, e.g. of dental adhesives, fixing cements or filling composites and of materials for inlays/onlays or teeth or of veneering materials for crowns and bridges. Such dental materials according to the invention are characterized by low polymerization shrinkage and good mechanical properties. In particular, they can even be used for patients allergic to (meth)acrylates. Furthermore, since the polymerized vinyl cyclopropanes according to the invention have no hydrolytically cleavable groups in the main chain, they prove to be stable even when they remain in the oral cavity for a relatively long time, which is naturally particularly advantageous when they are used as a dental material.

Preferred dental materials according to the invention contain the following components (a), (b), (c) and/or (d):
  (a) up to 99 wt. %, preferably 10 to 80 wt. % and particularly preferably 20 to 70 wt. % of the multifunctional vinyl cyclopropane derivatives according to the invention,
  (b) 0.01 to 5 wt. %, particularly preferably 0.1 to 2.0 wt. %, of an initiator,
  (c) 0 to 80 wt. %, preferably 0 to 60 wt. % and particularly preferably 0 to 50 wt. % of radically polymerizable comonomers,
  (d) 0 to 90 wt. %, particularly preferably, depending on the application, 0 to 20 wt. % in the case of adhesives, 20 to 60 wt. % in the case of cements and 60 to 85 wt. % in the case of filling composites, of fillers.

The invention is explained in more detail below with reference to examples.

EXAMPLES

Example 1

Synthesis of 2-vinyl cyclopropane-1,1-dicarboxylic acid monomethyl ester (1)

36.8 g (0.2 mol) of 2-vinyl cyclopropane-1,1-dicarboxylic acid dimethyl ester, obtainable from malonic acid dimethyl ester and trans-1,4-dibromobut-2-ene (cf U.S. Pat. No. 4,713,478 and U.S. Pat. No. 4,713,479), are dissolved in 65 ml of methanol in a 100 ml two-necked flask with a thermometer, magnetic stirrer and $CaCl_2$ tube, and the solution is cooled to ca 50° C. with iced water. Then 13.3 g (0.2 mol) of KOH are added in portions in such a way that the temperature does not rise above 15° C. In order to complete the reaction, stirring is continued for 12 hours, and then volatile components are removed in a rotary evaporator in vacuo (50 mbar) at 50° C. The oil obtained (ca 43 g) is dissolved in 50 ml of water and is adjusted to a pH of ca 2–3 with concentrated hydrochloric acid accompanied by cooling. The organic phase is taken up in 100 ml of diethyl ether, extracted twice more with in each case 100 ml of diethyl ether, and the combined ether phases are dried over anhydrous $Na_2SO_4$. The solution is stabilized with 0.01 g of hydroquinone monomethyl ether, concentrated in vacuo and dried under a medium high vacuum. The result is 28.2 g (83% yield) of a colourless liquid.

Elemental analysis: $C_8H_{10}O_4$ Calc.: C 56.47 H 5.92 (170.17) Found: C 56.60 H 5.82

IR (Film, $cm^{-1}$): 665 (w), 729 (w), 769 (w), 806 (w), 838 (w), 863 (w), 921 (m, sh), 958 (w), 992 (w), 1145 (s), 1209 (s, sh), 1289 (m), 1333 (s, sh), 1440 (s, sh), 1737 (s, sh, sh), 2957 (m), 3018 (m, b, sh).

$^1$H—NMR (90 MHz, $CDCl_3$): 1.93 and 2.03 (s, 2x 1H, $CH_2$-cyclopropane); 2.88–2.90 (q, 1H, CH-cyclopropane); 3.86 (s, 3H, $CH_3$); 5.18–5.69 (m, 3H, CH=$CH_2$); 12.30 (s, 1H, COOH, H/D exchange).

Example 2

Synthesis of 1,1,1-tris[(2-vinyl cyclopropane-1-carboxylic acid methyl ester-1-carbonyloxy)methyl]propane (2)

9.45 g (55.6 mmol) of the ester (1) prepared in Example 1, 2.5 g (18.7 mmol) of 1,1,1-tris(hydroxymethyl)propane, 0.061 g (0.5 mmol) of 4-dimethylaminopyridine (DMAP) are dissolved in 40 ml of absolute methylene chloride in a 100 ml two-necked flask with thermometer and $CaCl_2$ tube, and the solution is cooled to 0° to 5° C. with iced water. 11.45 g (55.6 mmol) of N,N'-dicyclohexylcarbodiimide (DCC) are added in portions, accompanied by stirring and further cooling, over a period of 1.5 hours. In order to complete the reaction, stirring is continued for a further 8 hours. The precipitated deposit is filtered off by suction, washed with some methylene chloride, and the combined organic phases are extracted in succession with 100 ml of 0.5N HCl, 60 ml of saturated sodium bicarbonate solution and 50 ml of saturated sodium chloride solution. After the methylene chloride has been distilled off in a rotary evaporator at 30° to 40° C., a colourless oil is obtained which is dissolved in 10 ml of acetone in order to separate off residual N,N'-dicyclohexyl urea and is concentrated again after filtration. After further drying under a medium high vacuum, 7.1 g (64% yield) of a clear, colourless, highly viscous oil is obtained.

Elemental analysis: $C_{30}H_{38}O_{12}$ Calc.: C 61.01 H 6.48 (590.62) Found: C 61.02 H 6.97

IR (Film, $cm^{-1}$): 786 (w), 917 (m, sh), 992 (m), 1060 (w), 1130 (s), 1208 (s), 1268 (s), 1330 (s, sh), 1438 (m), 1520 (w), 1650 (w, sh), 1732 (s), 2954 (m, sh)

$^1$H—NMR (90 MHz, $CDCl_3$): 0.90 (t, 3H, $CH_3CH_2$); 1.30–1.85 (m, 8H, $CH_2$-cyclopropane+$CH_2CH_3$); 2.55–2.75 (q, 3H, CH-cyclopropane); 3.77 (s, 9H, $CH_3O$); 3.93–4.31 (q, 6H, $CH_2O$); 5.11–5.58 (m, 9H, CH=$CH_2$).

Example 3
Synthesis of 1,2-bis(2-vinyl cyclopropane-1-carboxylic acid methyl ester-1-carbonyloxy)ethane (3)

The procedure is analogous to that of Example 2, and a solution of 6.8 g (0.04 mol) of ester (1), 1.25 g (0.02 mol) of absolute ethylene glycol and 0.061 g (0.5 mmol) of DMAP in 20 ml of methylene chloride is reacted with 8.25 g (0.04 mol) of DCC. The oil obtained is distilled under a medium high vacuum accompanied by the addition of some phenothiazine, whereupon 4.1 g (56% yield) of a colourless oil (b.p.$_{0.01\ mbar}$=155° to 160° C.) are obtained.

Elemental analysis: $C_{18}H_{22}O_8$ Calc.: C 59.01 H 6.05 (366.37) Found: C 59.30 H 6.30

IR (Film, $cm^{-1}$): 786 (w), 920 (w), 1132 (s), 1208 (s), 1270 (s), 1332 (s, sh), 1439 (m), 1645 (w), 1732 (s), 2956 (w, sh).

$^1$H—NMR (90 MHz, $CDCl_3$): 1.52–1.83 (m, 2×2H, $CH_2$-cyclopropane); 2.48–2.80 (q, 2×1H, CH-cyclopropane); 3.75 (s, 2×3H, $CH_3$); 4.40 (s, 4H, $OCH_2C$—$H_2O$); 5.12–5.60 (m, 2×3H, CH=$CH_2$).

Example 4
Synthesis of bis(2-vinyl cyclopropane-1,1-dicarboxylic acid methyl)resorcinyl ester (4)—(synthesis variant A)

The procedure is analogous to that of Example 2, and a solution of 17.0 g (0.1 mol) of ester (1), 5.5 g (0.02 mol) of resorcinol and 0.3 g (2.5 mmol) of DMAP in 60 ml of methylene chloride is reacted with 20.6 g (0.1 mol) of DCC. The oil obtained after the methylene chloride has been distilled off is dried under a medium high vacuum. After standing for several days, the product (15.2 g, 73% yield) becomes solid, differential scanning calorimetry (DSC) showing a melting range of 30°–80° C.

Elemental analysis: $C_{22}H_{22}O_8$ Calc.: C 63.76 H 5.35 (414.41) Found: C 63.51 H 5.55

IR (Film, $cm^{-1}$): 460 (w), 677 (m), 714 (w), 792 (m, sh), 829 (w), 918 (s), 962 (m), 997 (m), 1026 (w), 1054 (m), 1131 (s), 1202 (s, sh), 1260 (s, sh), 1324 (s, sh), 1440 (s), 1485 (m), 1600 (m), 1638 (m), 1730 (s), 1755 (s), 2955 (m, sh), 3011 (w), 3090 (w), 3460 (w, b).

$^1$H—NMR (90 MHz, $CDCl_3$): 1.65–2.03 (m, 4H, $CH_2$-cyclopropane); 2.60–2.85 (q, 2H, CH-cyclopropane); 3.82 (s, 6H, $CH_3$); 5.18–5.69 (m, 6H, CH=$CH_2$); 7.00–7.55 (m, 4H, CH-aromatic).

Example 5
Synthesis of bis(2-vinyl cyclopropane-1,1-dicarboxylic acid methyl)resorcinyl ester (4)—(synthesis variant B)
1st stage
bis(malonic acid methyl)resorcinyl ester A solution of 22.2 g (0.2 mol) of resorcinol, 44.5 g (0.44 mol) of triethylamine and 2.48 g (0.02 mol) of DMAP in 200 ml of absolute THF is introduced into a 750 ml sulphonation flask with a mechanical stirrer, thermometer, calcium chloride tube and dropping funnel, and a solution of 74.4 g (0.53 mol) of malonic acid monomethyl ester chloride in 200 ml of THF is added dropwise within 1 hour at 0° to 5° C. accompanied by good stirring. The mixture is allowed to warm up to room temperature, stirring of the reaction mixture continues for another 5 hours, the precipitated triethylamine hydrochloride is filtered off with suction, washed with 200 ml of ether, and the combined organic phases are extracted 5× with 100 ml of 1N HCl, 8× with 100 ml of 10% $Na_2CO_3$ solution and 5× with 100 ml of saturated NaCl solution until a neutral pH is reached. It is then dried over anhydrous $Na_2SO_4$, concentrated in a rotary evaporator and dried under a medium high vacuum until a constant weight is obtained. The crude product obtained (34.5 g) is purified by column chromatography, whereby 9 g (yield 15%) of pure product is obtained.

Elemental analysis: $C_{14}H_{14}O_8$ Calc.: C 54.20 H 4.55 (310.26) Found: C 54.64 H 4.47

$^1$H—NMR (90 MHz, $CDCl_3$): 3.60 (s, 4H, $CH_2$); 3.77 (s, 6H, $CH_3$); 7.0–7.5 (m, 4H, CH-aromatic).

2nd stage
bis(2-vinyl-cyclopropanedicarboxylic acid methyl) resorcinyl ester (4)

12.44 g (30.5 mmol) of sodium hydride as a 60% dispersion in oil are introduced into a 250 ml three-necked round flask with reflux condenser and thermometer and washed under argon with 50 ml of absolute petroleum ether. The petroleum ether is then decanted. This procedure is repeated twice, and finally 6.1 g (27.8 mmol) of trans-1,4-dibromo-2-butene and 90 ml of absolute THF are added. After that, a solution of 4.3 g (13.9 mmol) of bis(malonic acid methyl) resorcinyl ester in 90 ml of THF is added dropwise under argon and at room temperature over a period of 30 minutes, and the reaction mixture obtained is stirred at 65° C. for 4 hours. The suspension obtained is then concentrated in a rotary evaporator at 45° C. until dry, the residue is taken up in 100 ml of diethyl ether and extracted 3× with 100 ml of saturated $Na_2CO_3$ solution and 4× with 100 ml of saturated NaCl solution. The yellow, clear ether phase obtained is dried over anhydrous $Na_2SO_4$ and concentrated in a rotary evaporator. The residue obtained (4.2 g) is stabilized with in each case 50 ppm of di-tert. butyl cresol and phenothiazine, dried for 24 hours under a medium high vacuum, and purified by means of flash chromatography. 2.4 g of product (43% yield) are obtained, the IR and $^1$H—NMR spectra being the same as those of monomer (4) according to Example 4.

Example 6
Radical homopolymerization of vinyl cyclopropane derivative (4)

1.005 g (2.4 mmol) of vinyl cyclopropane derivative (4) are treated with 95 mg (0.06 mmol) of azobis (isobutyronitrile), degassed in a Schlenk vessel and then polymerized under argon at 65° C. The polymerization is discontinued after 15 hours by cooling and addition of 20 ml of chloroform. A polymerization shrinkage of merely ca 9.5 vol. % was calculated from the difference in density of monomer and insoluble polymer (proportion of gel 19.5%).

Example 7

Preparation of a dental cement based on vinyl cyclopropane derivative (4)

Composite fixing cements A) based on a conventional methacrylate mixture, B) containing a conventional monofunctional vinyl cyclopropane and C) containing the difunctional vinyl cyclopropane derivative (4) according to the invention were prepared. The cements had the compositions shown in Table 1. Test pieces were prepared from the cements and were irradiated twice for 3 minutes with a dental light source, namely Spectramat (Vivadent).

It can be seen from Table 2 that material A with the conventional methacrylate mixture has the greatest polymerization shrinkage. Material C, on the other hand, is superior to materials A and B both in terms of mechanical properties and in polymerization shrinkage.

TABLE 1

|  | Cement composition | | |
| --- | --- | --- | --- |
| Components | (A) Proportions (wt. %) | (B) Proportions (wt. %) | (C) Proportions (wt. %) |
| Urethane dimethacrylate[1] | 31.6 | 31.6 | 31.6 |
| Dodecanediol dimethacrylate | 7.80 | — | — |
| Mono(vinyl cyclopropane)[2] | — | 7.80 | — |
| Bis(vinyl cyclopropane) (4) | — | — | 7.80 |
| Aerosil OX-50[3] | 41.42 | 41.42 | 41.42 |
| Ytterbium trifluoride[4] | 18.70 | 18.70 | 18.70 |
| Camphor quinone | 0.24 | 0.24 | 0.24 |
| N,N-diethyl-3,5-di-tert.-butyl aniline | 0.23 | 0.23 | 0.23 |
| 3,5-di-tert.-butyl cresol | 0.01 | 0.01 | 0.01 |

[1] urethane dimethacrylate prepared from 2 mol of 2-hydroxyethyl methacrylate and 1 mol of 2,2,4-trimethylhexamethylene diisocyanate-1,6.
[2] 1,1-bis(phenoxycarbonyl)-2-vinyl cyclopropane prepared in an analogous manner to the literature (cf J. Sugiama et al. Macromolecules 27, (1994) 5543).
[3] pyrogenic silica from Degussa.
[4] from Rhone-Poulenc.

TABLE 2

|  | Cement properties | | |
| --- | --- | --- | --- |
| Material property | A | B | C |
| Polymerization shrinkage (vol. %) | 4.9 | 2.0 | 1.0 |
| Flexural strength according to ISO 4049 (MPa) | 86 | 49.5 | 88.5 |
| Flexural E modulus according to ISO 4049 (GPa) | 3.19 | 1.73 | 4.44 |

We claim:

1. Multifunctional vinyl cyclopropane derivatives of the following general formula (I), stereoisomers thereof and mixtures of such stereoisomers

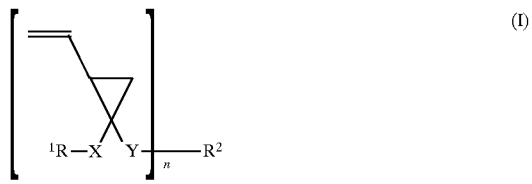

where $R^1$, $R^2$, $R^3$, $R^4$, X, Y and n independently of one another have the following meanings:

$R^1$=H, $C_1$ to $C_{12}$ alkyl or $C_6$ to $C_{14}$ aryl wherein the $C_1$ to $C_{12}$ alkyl and the $C_6$ to $C_{14}$ aryl optionally are substituted with OH, a halogen, a $C_1$ to $C_6$ alkoxy, or COOH;

$R^2$=n-times substituted $C_1$ to $C_{12}$ alkylene which can be interrupted by O, S, N, or NH, or n-times substituted $C_6$ to $C_{14}$ arylene;

X=CO, CO—O, CO—S, CO—$NR^3$, $SO_2$, or is absent where $R^3$=H, $C_1$ to $C_{12}$ alkyl or $C_6$ to $C_{14}$ aryl;

Y=CO, CO—O, CO—S, CO—$NR^3$, $SO_2$, where $R^4$=H, $C_1$ to $C_{12}$ alkyl or $C_6$ to $C_{14}$ aryl; and n=2 to 6 with the exception that when n=2, $R^2$=n-times substituted $C_6$ arylene.

2. Vinyl cyclopropane derivatives according to claim 1, wherein the variables of the formula (I) independently of one another have the following meanings:

$R^1$=H, $C_1$ to $C_6$ alkyl or $C_6$ aryl;

$R^2$=n-times substituted $C_1$ to $C_{12}$ alkylene, $C_6$ to $C_{14}$ arylene or $C_6$ to $C_8$ cycloalkylene;

X=CO—O;

$R^3$=H or $C_1$ to $C_3$ alkyl;

Y=CO—O;

$R^4$=H or $C_1$ to $C_3$ alkyl; and/or n=2 or 3.

3. A process for the preparation of the vinyl cyclopropane derivatives according to claim 1, wherein (A) a monovinyl cyclopropane derivative of the formula (IIA)

is reacted with an n-times functionalized coupling component of the formula (IIB)

with formation of the multifunctional vinyl cyclopropane derivatives of the formula (I), or (B) a compound of the formula (IIIA)

is reacted with an n-times functionalized coupling component (IIB)

$Z_nR^2$     (IIB)

with a formation of an intermediate of the formula (IIIB)

(IIIB)

and then (IIIB) is reacted with 1,4-dibromobut-2-ene with formation of the multifunctional vinyl cyclopropane derivatives of the formula (I),
where
T=H or halogen and Z=a leaving group and the remaining variables are as defined in claim 1.

4. A process according to claim 3, wherein Z=OH, $NH_2$ or halogen.

5. Polymers and copolymers, which can be obtained by polymerization or copolymerization of the multifunctional vinyl cyclopropane derivatives according to claim 1.

* * * * *